US 6,867,900 B2

(12) United States Patent
Weisbuch et al.

(10) Patent No.: US 6,867,900 B2
(45) Date of Patent: Mar. 15, 2005

(54) SUPPORT FOR CHROMOPHORIC ELEMENTS

(75) Inventors: Claude Weisbuch, Paris (FR); Henri Benisty, Paris (FR)

(73) Assignee: Genewave, Evry (FR)

(*) Notice: Subject to any disclaimer, the term of this patent is extended or adjusted under 35 U.S.C. 154(b) by 194 days.

(21) Appl. No.: 10/074,916

(22) Filed: Feb. 12, 2002

(65) Prior Publication Data

US 2002/0182716 A1 Dec. 5, 2002

Related U.S. Application Data

(63) Continuation of application No. PCT/FR01/02645, filed on Aug. 21, 2001.

(51) Int. Cl.[7] .............................. G02F 1/00; G02F 1/07; G02B 27/42; H01S 3/10; H01L 31/00
(52) U.S. Cl. ....................... 359/321; 359/260; 359/558; 372/20; 372/45; 372/50; 250/214.1
(58) Field of Search .................. 359/321, 260, 359/558, 566, 619; 385/24, 31, 32, 36; 372/20, 25, 26, 45, 50, 92, 96, 98, 102; 250/214.1, 338.1, 338.4; 257/21, 25, 103, 436; 356/246, 352, 519, 454

(56) References Cited

U.S. PATENT DOCUMENTS

| 4,647,544 | A | | 3/1987 | Nicoli et al. |
| 4,935,939 | A | * | 6/1990 | Liau et al. ..................... 372/98 |
| 5,255,067 | A | | 10/1993 | Carrabba et al. |
| 5,550,373 | A | * | 8/1996 | Cole et al. ............... 250/338.1 |
| 6,008,892 | A | | 12/1999 | Kain et al. |
| 6,380,531 | B1 | * | 4/2002 | Sugihwo et al. .......... 250/214.1 |
| 6,459,716 | B1 | * | 10/2002 | Lo et al. ....................... 372/50 |
| 6,577,660 | B1 | * | 6/2003 | Muroya ........................ 372/45 |
| 6,614,060 | B1 | * | 9/2003 | Wang et al. ................ 257/103 |

FOREIGN PATENT DOCUMENTS

| DE | 38 32 185 A1 | 3/1990 |
| EP | 1 085 315 A1 | 3/2001 |
| WO | WO 00/12123 | 3/2000 |

* cited by examiner

*Primary Examiner*—Loha Ben
(74) *Attorney, Agent, or Firm*—Alston & Bird LLP (57) ABSTRACT

A device for supporting chromophoric elements comprises support means (1) for receiving, on an upper face (24), chromophoric elements (5) that can emit light under selected conditions, and means for concentrating light (3) to recover the light emitted by each chromophoric element (5) in a portion of the region around it and "deliver" that recovered light to a collecting device.

47 Claims, 6 Drawing Sheets

SUPPORT FOR CHROMOPHORIC ELEMENTS

CROSS-REFERENCE TO RELATED APPLICATIONS

This application is a continuation of pending PGT International Application PCT/FR01/02645, filed Aug. 21, 2001, designating inter alia the United States.

The present invention relates to improving the detection of chromophoric or chromogenic signals directly or indirectly connected to chemical or biological cells, molecules or macromolecules fixed to supports.

The term "chromophoric signal" or "chromogenic signal" means any light signal emitted directly or indirectly after excitation by suitable light or after enzymatic transformation of a chromogenic substrate. The category of chromophoric or chromogenic signals includes colorimetric, photoluminescent, fluorescent, chemoluminescent and bioluminescent signals and the like. Such signals are emitted either directly by the molecules of interest or by elements added to them and/or grafted onto them, such as colorant molecules or certain types of semiconducting nanostructures such as quantum wires or boxes.

The technologies used in cell and molecular biology to detect and quantify the presence of a molecule usually exploit such signals and are detected by spectrometers, fluorimeters or luminometers equipped with photomultipliers.

The term "molecule" as used here means any type of molecule or macromolecule, isolated or bonded to a structure or to another molecule. Examples that can be cited are nucleic acids or oligonucleotides, proteins or polypeptide sequences and antibodies or fragments thereof. The term "molecule" can also mean chemical molecules with a particular affinity for a specific ligand. Examples that can be mentioned are the molecules obtained from high throughput syntheses and their selection using combination chemistry techniques.

The accessibility of biological material and the search for the presence of a particular molecule in a complex mixture have led to the development of miniaturized techniques that employ "chips", "microarrays" and "macroarrays". The molecules to be investigated or to be quantified (targets) are brought into the presence of specific known ligands (probes) fixed on a support or a substrate that is currently formed from glass, silica, nylon or a metal. A target is detected when it couples to a fixed probe (or specific ligand) because the target carries a chromophore (it is possible for the probe to carry the chromophore).

The term "support" or "substrate" as used here means any means that can support chromophoric elements. As a result, it may be a monolayer structure or a multilayer structure. The monolayer or one of the layers of the multilayer can be a substrate that is commercially available and possibly modified.

The respective arrangements of targets, probes and chromophores are interchangeable. This text refers to probes integral with a support and with which the targets interact, but it is possible for the targets to be integral with the support, and the probes could then interact therewith.

The probes can be fixed on their supports in different manners. Examples are chemical addressing, electrochemical addressing, or addressing using a technology similar to the inkjet technology used in printers.

A detailed review of that subject can be found in the article by F. Bertucci et al., Human Molecular Genetics (1999), 8, n° 9, pp. 1715–1722.

The sensitivity of the detection means currently used necessitates the presence of at least $10^4$ molecules of a single category to obtain a significant response. Further, as more and more probes are being mounted on ever smaller supports, it is becoming particularly difficult to detect the origin of luminescent signals or colorimetric signals generated after coupling or probe/target hybridization.

Conventional solutions for improving measurement sensitivity have up to now consisted of enhancing either the emitted signal, for example using radioactive targets, or the quantity of material that can be hybridized or coupled. However, such solutions are not satisfactory.

Other solutions require optical systems with a very wide numerical aperture and/or immersed systems, which are incompatible with the rapid scanning requirements of large arrays.

U.S. Pat. No. 6,008,892 describes a device for supporting chromophoric elements which comprises a rigid base with a reflective surface, for example metal, covered with a transparent layer, for example silica, on which the chromophoric elements are fixed. The optical pathway between the reflective surface of the base and the upper face of the transparent layer is an odd multiple of one quarter wavelength of the excitation light for the chromophoric elements, such that the standing wave of the incident excitation light has an antinode at the level of the chromophoric elements. Chromophore excitation is then a maximum. The reflective base can also enhance collection of the fluorescence emitted in response to excitation, by practically doubling the solid angle over which fluorescence is collected by a microscope system.

The aim of the present invention is to further improve detection of the light emitted by chromophoric elements in response to light excitation.

To this end, the invention provides a device for supporting chromophoric elements of the type defined above, which can concentrate at least a portion of the light emitted by the chromophoric elements in a selected region of space, to allow it to be captured. The term "concentrate" as used here means firstly, recovering the light emitted by the chromophoric elements in a portion of the region around it, then constraining that recovered light to reach one or more collection zones.

Thus, the invention provides a device for supporting at least one chromophoric element, comprising a substrate having an upper surface on which said chromophoric element is fixed and means for enhancing the quantity of light emitted by the chromophoric element towards a collecting device, said means forming part of a group comprising reflective means placed in the substrate at a distance from its upper surface, characterized in that this group also comprises:

microlenses each associated with a chromophoric element and functioning in transmission or in reflection;

diffraction means placed at a distance from the chromophoric element or elements and functioning in transmission or in reflection;

first reflective means and second reflective means parallel to each other and placed either side of the chromophoric element or elements to define an asymmetric resonant cavity;

a planar wave guide formed in the substrate below the upper surface carrying the chromophore or chromophores, to capture a portion of the light emitted by the chromophore or chromophores into the substrate and/or to supply excitation light;

a configuration of the upper surface of the substrate, formed as wells with a reflective bottom and filled with a material with a suitable index each receiving a chromophoric element;

planar resonators formed in the upper surface of the substrate;

and in that the means enhancing the quantity of light emitted by the chromophoric element or elements comprise at least one of the means belonging to said group.

The device of the invention thus aims to modify the optical environment of each chromophoric element such that a large proportion of the light it emits is collected. The yield is improved, along with the sensitivity of molecule detection tests.

In addition, for certain particular applications requiring excitation light for the chromophoric elements, the invention allows the excitation intensity to be reduced.

In some embodiments, this invention can also improve rejection of the excitation light collected in the detector, and as a result improves the signal-to-noise ratio (S/N).

In some embodiments, the invention can also reinforce optical excitation of the chromophores in addition to reinforcing collection of the light emitted by said chromophores.

A number of embodiments can be envisaged, depending on whether the modification to the environment of the chromophore relies on geometrical optics and/or wave optics effect.

In the field of geometrical optics, for example, where propagation of emitted and/or incident radiation (excitation radiation) is governed by the laws of geometrical optics, there may be provided:

- a first, "far" mirror integral with (or formed in) a substrate at a distance (d) from the chromophores, the distance being large with respect to the emission wavelength ($\lambda$), i.e., satisfying the criterion $d > n\lambda/2NA^2$ (where "NA" is the numerical aperture of the collecting lens and "n" is the index of the medium between the mirror and the chromophores), and intended to reflect the light emitted by the chromophoric elements towards the selected region in space. The first far mirror can be produced in the form of a stack of dielectric layers;
- microlenses each associated with a chromophoric element, and which can function in transmission or in reflection, i.e., by focusing forwards or backwards, as is the case with a Fresnel mirror;
- small wells, filled with a material with a suitable index (preferably high) and the bottom of which is reflective, and each capable of receiving at least one chromophoric element onto this filling material;
- diffraction means functioning in transmission or in reflection and placed at a selected distance from the chromophoric elements;
- if the chromophores emit into a planar waveguide (the chromophores are not necessarily placed in this guide), channels defining a blazed grating to collect the light emitted by the chromophoric elements in the direction of the support means and to guide this light towards the collecting device;
- parallel linear structures produced in the upper forward face of the substrate in the form of channels (or grooves) or ribs, which may be U, V or parabolic in shape, filled with a material with a suitable index, with a reflective base, capable of receiving at least one chromophoric element on this filling material (between them, at their tops or at their centers);
- a planar waveguide for guiding chromophore excitation light by minimizing diffusion of this light into the neighboring media;

in the absence of a collection waveguide, it is possible to provide a matrix of charge coupled detecting (CCD) devices associated with the rear face of the substrate, at least some of the detecting elements being electronically addressed in correspondence with at least one chromophoric element. In this case, between the matrix and the substrate, a layer forming an interference mirror is advantageously provided, arranged so as to reject chromophoric element excitation light. It is also possible to couple the pixels from a CCD detector either to sites carrying active or empty chromophoric elements or non active chromophoric elements, or to sites having a reference activity signal, to obtain, by differential measurement of the pixels from the CCD detector, the signal of the active chromophore with an increased S/N ratio by subtracting the background noise and stray excitation signal.

In the wave optics field, for example, where interference phenomena are employed to reinforce or reduce optical waves, it is possible to have:

- a first reflector (or mirror) known as the "near" mirror analogous to that for geometrical optics but placed at a distance (d) from the chromophores so that said reflector provides an interference effect to amplify collection of the light emitted into the support (d satisfies the relationship $d < n\lambda/2NA^2$), and coupled to the excitation waves arriving at the chromophores with a non zero angle of incidence with respect to the normal to the support. This angle of incidence also reinforces excitation when double resonance exists, i.e., coincidence between the antinodes in the field for the two excitation wavelength ($\lambda_{exc}$) and emission wavelengths ($\lambda_{em}$). Detection remains centered on the normal to the support;
- this first mirror, placed below the chromophoric elements, can be combined with a second semi-reflective mirror placed above these chromophoric elements, substantially parallel to the first mirror and at a selected distance from it to define an asymmetric resonant cavity, in particular of the Fabry-Pérot type, delivering the light collected through the second mirror. In a variation, the second mirror or exit mirror can be below and the most reflective mirror at the emitted wavelength can be above, this latter mirror possibly being substantially transparent at the excitation wavelength. In general, in the two cases, a double resonance condition analogous to that of the near mirror can be satisfied, taking distance d to be that which separates the chromophores from the most reflective mirror. The second mirror can be deposited directly either on the substrate or on the entrance face of an optical collector, or it may be constituted by the diopter of an existing entrance face;
- a planar waveguide capturing a large fraction of the light from the chromophores emitted into the support, and preferably provided with the means mentioned above for channeling the captured light towards the collecting device;
- a planar resonator formed in the substrate around each chromophoric element, intended to store the electromagnetic energy from the field it induces and arranged so that the associated chromophoric element is substantially positioned on an antinode in the electromagnetic field. It may comprise concentric circular channels or grooves (at least two) at the center of which is placed a chromophoric element. It may also comprise rectangular or parallel channels or grooves defining a lamellar grating;

a two-dimensional (2D) or three-dimensional (3D) array or holes or columns defining a photonic crystal, preferably of the photon band gap type to control light propagation in its region, which may go so far as to forbid it;

means for concentrating light that cause localized resonances by local reinforcement of the electromagnetic field induced by the presence of nanometric structures (for example islets) which may or may not be regular, or nanometric holes, produced in selected metals, in particular silver (Ag). These nanometric islets or holes are capable of enhancing emission and also excitation such as in surface enhanced Raman scattering (SERS);

means for concentrating light comprising an asymmetric resonant cavity, in particular of the Fabry-Pérot type, integrated into the substrate below the upper layer, this layer being at least partially permeable, vertically and/or laterally, to allow the chromophoric elements to migrate towards selected sites relative to the resonant cavity. This cavity is preferably defined by first and second mirrors, and the upper layer is preferably produced in a porous material, for example silica gel. Further, the upper layer can comprise holes at selected locations to encourage migration of the chromophoric elements towards the sites.

Certain of the embodiments described above can be taken in combination, to further improve light collection.

The invention concerns all fields in which the device described above can be used, in particular in biology, biochemistry and chemistry.

More particularly, it concerns the use of a device of the type described above and the use of biochips intended to allow the detection of pairs of target and probe oligonucleotides, such as DNA strands, detecting an interaction between target polypeptide sequences or proteins, labeled with a molecule that is capable of directly or indirectly emitting chromophoric or chromogenic signals, in particular luminescent, fluorescent or colorimetric signals, and probe polypeptide sequences or proteins, and detecting the interaction between probe chemical molecules and target chemical molecules.

Other characteristics and advantages of the invention will become apparent from the following detailed description and the accompanying drawings, in which.

The accompanying drawings illustrate definitive embodiments. As a result, they not only serve to describe the invention, but if necessary they also contribute to its definition.

In the following description, reference will be made to devices for supporting chromophoric elements comprising at least one support on which multiple zones are produced to receive probes which are to be coupled to targets. In the described application, the targets and probes are oligonucleotides such an DNA strands. However, the invention is not limited to that application; the targets and probes could be proteins or polypeptide sequences, or more generally any type of chemical, biochemical or biological molecule.

The device of the invention is intended to recover at least a fraction of the light photons emitted by chromophoric elements into a part of the region surrounding them, so that they are delivered to a selected region in space in which a collecting device is disposed, such as the objective of a microscope coupled to a photodetector, for example a photomultiplier or a matrix of photodetecting elements, for example of the CCD (charge coupled device) type.

To recover photons, the support device comprises means for concentrating light which can be classified into two different categories depending on whether they function in accordance with the laws of wave optics or of geometrical optics.

Figure 1:
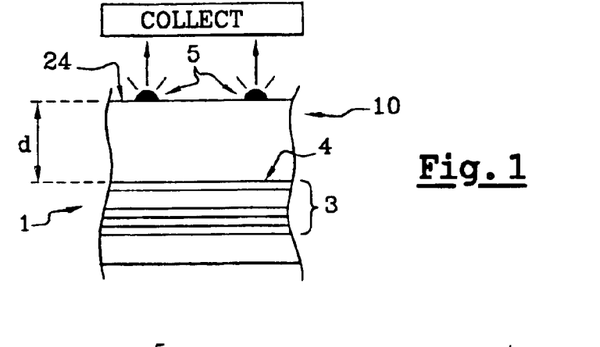
FIG. 1 is a highly diagrammatic cross sectional view of a device in accordance with the invention, with a "far" mirror formed solely from dielectric layers, or hybrids of dielectric and metallic layers.

Reference should firstly be made to FIG. 1 to describe an embodiment of the device of the invention functioning in accordance with the laws of geometrical optics.

The device comprises a support 1 formed from a substrate 2 in which a reflective mirror 3 is formed at a distance (d) from its upper face 24. The mirror can be formed by depositing a layer that is highly reflective at the working wavelengths (emission wavelengths of the chromophores). In a variation and as illustrated, the mirror is constituted by a multiplicity of dielectric layers 3. The substrate 2 and the dielectric layers 3 can be produced front semiconductor materials or from oxides or glasses. As an example, for an emission wavelength ($\lambda_{emis}$) of the order of 600 nanometers (nm), layers of $SiO_2$ can be selected (with a refractive index n1=1.5) and with a thickness e1=$\lambda$/4n1=100 nm, and layers of $TiO_2$ (with a refractive index n2=2.5) with thickness e2=$\lambda$/4n2=60 nm. In this example, 2 to 10 pairs of layers are repaired, with an $SiO_2$ layer as the first layer.

However, other materials can be envisaged, such as nitrides ($Si_3N_4$) or organic or organometallic polymers, the polymers possibly being either amorphous (isotropic material) or "orientated" and birefringent. More details regarding the particularly advantageous reflective properties of birefringent polymer layers, in particular when using two polarizations, can be found by referring to the article by Weber et al., in Science, vol. 287, p. 2451, Mar. 31, 2000.

In the illustrated embodiment, the mirror is "far" so as to function in accordance with the laws of geometrical optics. The term "far mirror" means any type of reflective structure functioning, because of its distance from the chromophores, in accordance with the laws of geometrical optics and not in accordance with the laws of wave optics (interference phenomena). In other words, the mirror is a distance d from chromophores 5, distance d satisfying the criterion: d>n$\lambda$/2NA$^2$; where "NA" is the numerical aperture of the objective collecting the light emitted by the chromophores at a wavelength (λ), and "n" is the index of the medium between the mirror and the chromophores.

Such a "far" mirror, which is reflective, can multiply by about two the number of photons collected substantially around the direction N normal to the upper face 24 of support 1, the angle of incidence of the excitation light on face 24 being any angle.

Once produced, the upper face 24 of support 1 first receives the different probes in the selected locations. The probes are fixed onto support 1 using addressing techniques that are known to the skilled person, which depends on the nature of the probes and on the upper surface 24 of support 1. As an example, it is possible to use a chemical addressing technique, or electrochemical addressing, or a technique similar to the inkjet technique employed in printers.

Supports 1 equipped with their probes are then brought into communication with the targets, for example by immersion, so that certain targets interact with certain probes. The term "interaction" as used here means any type of coupling or hybridization or pairing that can form target/probe pairs in a relatively durable manner.

As an example, the targets are DNA strands provided with luminescent markers. The term "luminescence" as used here means any type of light mission, induced or spontaneous, such as photoluminescence, fluorescence or phosphorescence. In certain applications for which it is not possible to fix luminescent markers onto the target or the probe, luminescence is locally ensured by structures onto which the target/probe pairs are fixed. This is particularly the case in certain semiconductor structures such as quantum wires and boxes (see the document by Bruchez et al., Science 281, p. 2013, Sep. 25, 1998), or colorants whereby the pair fixed thereon acts as a luminescence destroyer or amplifier. In this case, the substrate (mono or multi-layer) can be produced from semiconductive materials.

In this invention, therefore, the term "chromophoric element" means any element that is capable of directly or indirectly emitting a chromophoric signal or a chromogenic signal, following excitation by a suitable light or after enzymatic transformation of a chromogenic substrate. It can thus be either a target/probe pair integral with the upper surface 24 of support 1 and which can spontaneously emit or be induced to emit light photons, or a three-dimensional structure which, once associated with a target/probe pair, emits light spontaneously or in an induced manner, or an element that is integral with the substrate and which, once associated with a target/probe pair, changes its behavior emitting much more or much less than in the absence of the pair, whether the emission is spontaneous or induced.

Thus, the invention aims to encourage collection of photons emitted by chromophores, and in particular all or a portion of the light that would be emitted in the direction of support 1. It should be remembered here that about 70% of the light emitted by the chromophores is lost in the substrate and the remaining 30% is not necessarily captured by the collecting device, because of limitations in the collection aperture.

In a variation, support 1 of the device can comprise microlenses that may or may not be structured and located substantially below each chromophore 5, functioning in transmission or in reflection (micromirror), i.e., by focusing forwards or rearwards, as is the case for Fresnel mirrors in particular. It is also possible to use diffractive devices placed at distances that are sufficiently large compared with the wavelength of the emitted light. Under these conditions, the diffraction means function in accordance with the laws of geometrical optics, and their characteristics (angles of incidence and emergence) are fixed by the laws of gratings.

One particular grating embodiment consists of redirecting the light using a synthesized holographic grating (i.e., resulting from calculating an optical transfer function using methods known to the skilled person). More details regarding the ability of these holographic gratings to redirect waves guided into a plane or outside a plane can be obtained by referring to Martinsson et al., IEEE Photon Tech. Letters 11, 503, 1999, and Larsson et al., SPIE Proc. 3626, 1999.

Figure 2A:
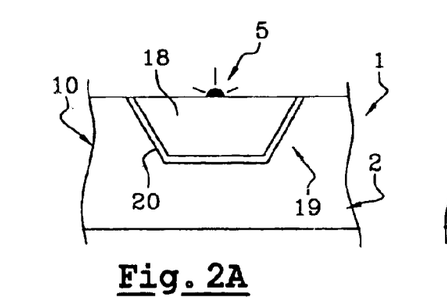
FIGS. 2A and 2B are highly diagrammatic cross sectional views of devices of the invention with mirrored wells.
Figure 2B:
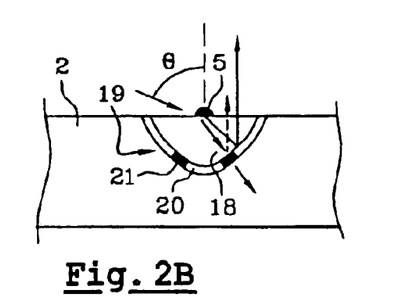

Reference should now be made to FIGS. 2A and 2B to describe a particularly advantageous further embodiment. In this embodiment, small wells 19 (or three-dimensional reliefs) are formed in the upper portion 10 of support 1. These reliefs can be produced using different techniques for defining patterns (such as lithography and serigraphy, e-beam exposure), followed by techniques for forming reliefs (such as chemical or dry engraving, using plasma, ion beam, plasma and/or reactive ion beam), and also directly by embossing.

After depositing a reflective layer 20 (or a multilayer assembly with reflective properties at the wavelengths of interest) on the bottom of each well 19, it is filled with a filling material 16 with an index n2, preferably a high index, then chromophore 5 is placed on the upper surface of the filling material 18, substantially in the focal point (center) of the well 19. A plurality (at least two) of chromophores can optionally be placed above the same well.

The reflective nature of the three-dimensional structures is produced by metallic or dielectric deposits. The wells are filled by any method suitable for the desired material, preferably a dielectric method. Flat filling can be envisaged, such as in the case of an epoxy resin that solidifies flat, or by flattening in the case of a convex deposit, or without intervention, for example in the case of a concave dielectric.

Preferably, as shown in FIG. 2B, wells 19 are parabolas of revolution, and the geometric focal point is located at the intended location for the chromophore (on filling material 18), to permit idealized collection of a maximum of the emitted light. Emission from a chromophore placed a few nanometers (nm) from a n1/n2 interface sends the light mainly into a cone with an angle spread between a critical angle $\theta c=\sin^{-1}(n1/n2)$ and $\theta c+10°$ or 20°. More details regarding this mechanism can be obtained from the articles by Lukosz W. and Kunz, R. E., J. Opt. Soc. Am. Vol. 67, pp. 1615–1619 (1977), Lukosz W., J. Opt. Soc. Am. Vol 69, pp. 1495–1503 (1979), and Lukosz W., Phys. Rev. B. vol. 22, pp. 3030–3038 (1980). The well can also be an ellipse of revolution, to form an upstream real image of the chromophore located at the downstream focal point. Facetted wells of revolution can also be envisaged, the facetting being n-dimensional, where n is 1 or more. It is also possible to produce wells with a three-dimensional facetting (n=3), when the material lends itself to chemical engraving revealing preferred crystal planes.

It is also possible to concentrate the emitted light with simple grooves, for example in the form of a U or a V, or parabolic or even elliptical.

In the embodiments described above, it is also possible to improve rejection of the excitation light by omitting to render reflective the regions of the wells illuminated by particular angles θ (including three dimensions). As an example, for a beam in a cone of revolution with an angle θ and a focal point located at the position of the chromophore, the reflective treatment must be omitted over a ring 21, over a parabola of revolution, and if possible this region 21 must be rendered non reflective, non diffusing, but rather, absorbing, for example. Under these conditions, it is possible to obtain strong rejection combined with a high signal rendering reflective only the projection of this angular region onto the well, by fixing an angle of excitation that is not in this angular window.

Since the absolute quantity of light emitted spontaneously or in an induced manner by chromophores 5 increases with the index n2 of the filling material 18 because of the higher probability of a radiative channel, which is proportional to a power of n2, materials with a high index n2 are preferably selected.

To detect channeled photons, the use of electronically addressed matrices of photodetecting elements is particularly advantageous, such as charge coupled devices or devices formed using metal-oxide semiconductor (MOS) technology, being the cheapest currently available matrix detectors.

Preferably, these detectors are used to directly form support 1 or substrate 2, which prevents any loss of light and retains radiation inclined beyond the critical angle of the support-air interface. With a detector separated from the support by a medium with a low index, such as air, these rays will be totally reflected and will not reach the detector.

Figure 7:
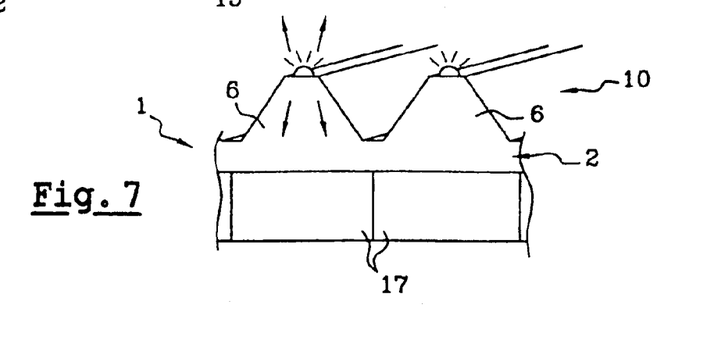
FIG. 7 is a highly diagrammatic cross sectional view of a device in accordance with the invention with a groove structure coupled with CCD type detection elements.

CCD matrices can be produced on a silicon substrate, for example, so that they function at visible wavelengths, in the near infrared, or even in the near ultraviolet. These matrices are resistant to certain heat treatments, fluid or other, necessary in the production of the device of the invention. Further, such photodetectors comprise photosensitive elements (or pixels) (as shown in the example of FIG. 7) the dimensions of which can be in the range from 5 micrometers ($\mu$m) to 50 $\mu$m and which, as a result, enable very high probe densities to be employed on that support.

When luminescence is induced, it may prove necessary to dispose of the photoexcitation light, which may saturate (or blind) or even destroy the photodetection elements. Two solutions can be envisaged. A first solution is suitable for cases in which luminescence decreases more slowly than the period between two acquisitions. In these cases, it is possible to carry out pulsed rapid photo-excitation to "empty" the detection pixels of the CCD matrix before acquisition. A second solution consists in adding mirrors, for example interference mirrors, or mirrors of another type (colored filters, for example) or a combination of mirrors of different types, strong rejectors of excitation radiation (with a typical value of less than $10^{-4}$, if possible less than $10^{-5}$), while providing a transmission window for the radiation from chromophores 5. Clearly, these two solutions can be combined together to further improve the collection results.

This means that microlenses or a mirror can be dispensed with, while retaining the possibility of carrying out complementary functions, of the wavelength filtering type, at the collecting device.

The signal-to-noise (S/N) ratio can also be improved using a differential method of the type described below. A first detection pixel is placed facing each chromophore, and one or more other detection pixels are placed to the side of this first pixel to collect the remainder of the emitted light which has not been concentrated by the means of the invention, or any stray light. A differential measurement of the signal received by the pixel associated with the chromophore and the signal received by the neighboring pixel or pixels produces a better S/N ratio and can dispense with various sources of noises and stray signals.

Figure 3A:
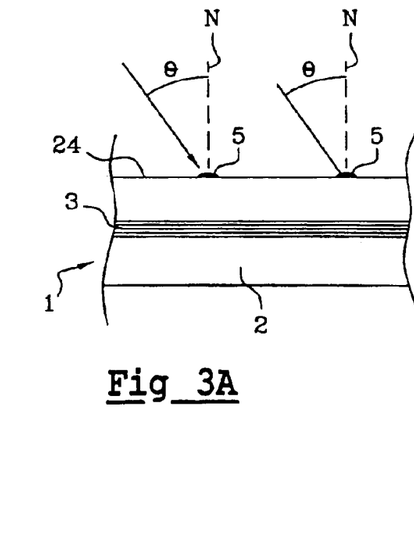
FIG. 3A is a highly diagrammatic cross sectional view of a device in accordance with the invention, with a "near" mirror coupled to a non zero angle of incidence excitation; the curves of FIGS. 3B and 3C respectively illustrate graphs of the luminescence intensity ($|E_{fluo}(Z)|^2$) and excitation intensity ($|E_{exc}(Z)|^2$) as a function of the side (or thickness) z.
Figures 3B, 3C:
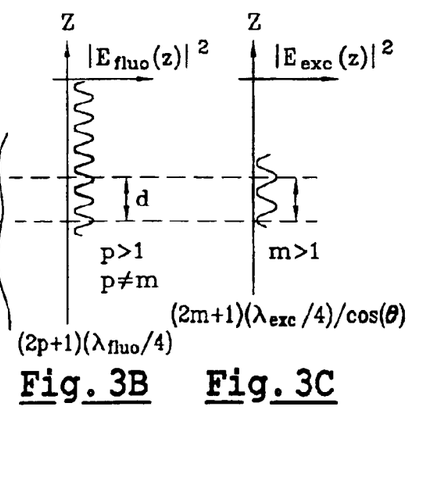

We now refer to FIGS. 3A to 3C to describe a further embodiment of a device of the invention, functioning in accordance with the laws of wave optics.

More precisely, in this embodiment we create double resonance to reinforce the collected light and excitation light. The first resonance concerns the emission wavelength, while the second resonance concerns the excitation wavelength. This double resonance is produced by determining the coincidence of the antinodes in the electric field for the two wavelengths, excitation and emission.

A support 1 is used of the type described above with reference to FIG. 1, i.e., comprising a reflective mirror 3 formed from dielectric or metallic layers. However, in contrast to the example of FIG. 1, where the mirror is a far mirror, in this embodiment the mirror is a "near" mirror. In other words, it is placed at a distance (d) from the chromophores that satisfies the criterion: $d < n\lambda/2NA^2$.

Under these conditions, an interference effect is produced that can enhance the collected energy by a factor of four. More details regarding this mechanism can be obtained from the article by Benisty et al., IEEE J. Quantum Electron, vol. 34, 1612, 1998.

This near mirror condition is combined with a condition regarding the angle of incidence $\theta$ of the excitation light with respect to the normal N to the upper surface of support 1 (concentrated light is collected substantially perpendicular to the upper surface of support 1).

The spacing a of the field antinodes at wavelength $\lambda$ in a medium with an index n illuminated by a wave the incidence of which in an external medium, with an index $n_{ext}$, is $\theta$, is given by:

$$a = (\lambda/2n)/\cos(\arcsin((n_{ext}/n)*\sin(\theta))).$$

$a_{exc}$ is the spacing of the antinodes for an excitation at an angle $\theta$, and $a_{fluo}$ is the spacing of the antinodes for fluorescence detected at $\theta_{fluo}$ (generally at about 0 degrees, but this angle can be offset to the middle of the collection window of the lens, i.e.: $\sin(\theta_{fluo}) = NA/2$.

The choice of excitation angle $\theta$ (for a conical beam) allows the spatial position of the antinode for the excitation light ($\lambda_{exc}$) to be adjusted and to achieve adequate spatial coincidence with the antinode of the emitted light ($\lambda_{fluo}$).

More precisely, $\theta$ must be found by satisfying the following condition:

$$(p+\tfrac{1}{2})*a_{exc} = (m+\tfrac{1}{2})*a_{fluo}$$

where p and m are the smallest possible. This is achieved by starting from a convenient low value for m of less than 20, and trying values of p that are lower than or equal to $p_o = m*(\lambda_{fluo}/\lambda_{exc})$, or a little higher if the penetration depths of the mirror vary rapidly with the wavelength in the region under consideration. Values of $\theta$ are found to increase as p decreases; we stop at the pair (m, p) that is the most convenient and the smallest, taking into account the other constraints on support manufacture.

For better adjustment, the penetration depths $a_{pen}$ into the mirrors must also be taken into account, as the mirrors are not ideal mirrors. These depths are only a small fraction of $\lambda$ for metals, but are given by $(\lambda/2n_{mean})*(n_{mean}/2\Delta n))$ for a multilayer Bragg mirror type stack, $n_{mean}$ being the mean of the indices of the two layers and $\Delta n$ being their difference in index.

The exact condition to be satisfied to find $\theta$ is then:

$$(p+\tfrac{1}{2})*a_{exc} - a_{pen}(\lambda_{exc}) = (m+\tfrac{1}{2})*a_{fluo} - a_{pen}(\lambda_{fluo})$$

It should be noted that in this case, optimization of the thicknesses and compositions of the reinforcing absorption layers does not in practice depend on the numerical apertures considered.

It is also possible to envisage that an assembly of layers could be anti-guiding as regards the plane of the chromophores 5, i.e., that the tendency of the modes that propagate in this assembly to capture the light emission is lower than a substrate with the same mean index as these layers. Photons that are not emitted in this assembly of layers are then found substantially in the collection cone, especially when this cone is quite large.

Figure 4A:
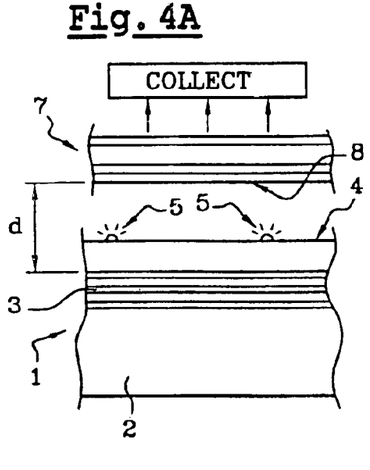
FIGS. 4A and 4B are highly diagrammatic cross sectional views of devices in accordance with the invention with a resonant cavity.

Reference should now be made to FIG. 4A to describe a further embodiment of a device of the invention, functioning in accordance with the laws of wave optics.

In this embodiment, a support 1 is provided of the type described above with reference to FIG. 3A, i.e., a substrate 2 comprising a near mirror, reflective, formed from dielectric layers 3, for example, and a second mirror 7, semi-reflective, placed above the chromophores at a set distance (d) from the upper surface 4 of the first mirror. The distance d between this upper surface 4 of the first mirror and the lower surface 8 of the second mirror 7, facing it, is selected so that the two mirrors define an asymmetric resonant cavity of the Fabry-Pérot type.

The distance (d1) between the first mirror and the chromophores is selected to ensure the presence of a field antinode at chromophores 5, and is thus substantially d1= $(m+\frac{1}{2})*\lambda_{fluo} - a_{pen}(\lambda_{fluo})$. The excitation angle $\theta$ can be selected in the same manner as indicated above for a simple mirror, and the most favorable of the values of $\theta$ are selected taking the properties of the second mirror into account.

The second semi-reflective mirror 7 allows photons emitted by chromophores 5 placed on the upper surface 4 of first mirror 3 to traverse it, and as a result to be detected by a collecting device (placed above the second mirror 7). Such a second semi-reflective mirror 7 can advantageously be formed by the lower face of an objective of the collector. It may be that face directly, or a coating deposited thereon. Since adjustment of the resonance wavelength with respect to the emission wavelength (tuning) must be quite accurate (of the order of about 1%), an adjuster can be provided on one of the elements of the device (for example the support or an external mirror) of the piezoelectric type controlled by an optical in situ measurement of resonance. Further, this adjuster can be envisaged to be coupled to the collecting device, or mounted so as to allow the surface of support 1 to be scanned.

In a variation, the second semi-reflective mirror 7 can be formed on the lower face of a coverslip of the type used for microscopic observations. Because of the very small dimensions of resonant Fabry-Pérot type cavities, typically $\lambda/2$, the coverslip can be placed over the chromophores 5, interposing a fluid (constituted, for example, by the biological sample itself or by a wetting liquid), and the cavity thickness is then controlled by controlling the pressure applied to the coverslip, which can optionally be coupled to an automatic optical control.

Figure 4B:
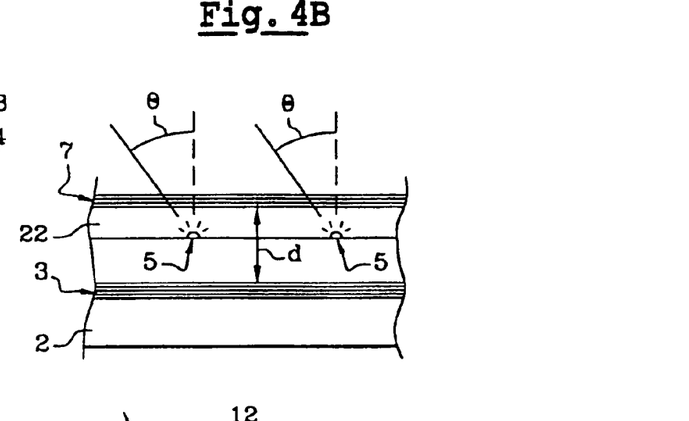

In a further embodiment of the invention, shown in FIG. 4B, the resonant cavity is made all of a piece, the upper layer and the upper mirror 7 being integral with the substrate 2, and the sites for positioning the chromophores 5 being located inside the structure at optically suitable positions, given above, relative to the resonant cavity. The resonant cavity is preferably of the asymmetric Fabry-Pérot type, and more generally delimited by two mirrors 3, 7 spaced apart by a distance (d) selected mainly as a function of the working wavelength and the materials used. These two mirrors are preferably of the type described above, i.e., in the form of a multilayer dielectric structure.

Access to the internal sites by the chromophores 5 is achieved by any means rendering the upper layer 22 at least partially permeable, vertically and/or laterally. As an example, porous materials such as silica gel can be used. These materials can also include holes to facilitate migration of the chromophores towards the internal sites.

Figure 5:
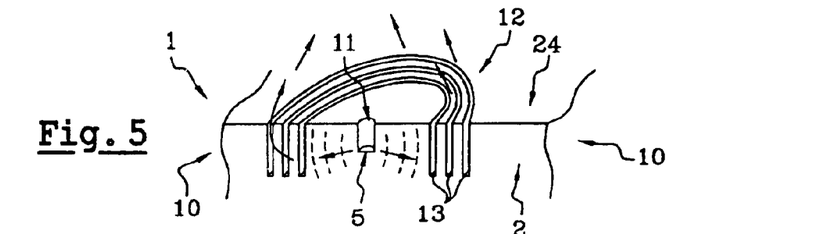
FIG. 5 is a highly diagrammatic cross sectional view of a device in accordance with the invention, with a planar resonator with grooves.

Reference should now be made to FIG. 5 to describe a further embodiment of a device of the invention, in which the light concentrating means function in accordance with the rules of wave optics.

In this embodiment, support 1 is formed from a substrate 2, the supper surface 24 of which comprises a multiplicity of holes 11 each intended to receive a target. The holes allow the chromophores to be placed in locations where the field of the resonator is a maximum. Their depth is between zero and the depth of the grooves of the resonator, described below. These holes are preferably arranged in a regular manner. To collect the light emitted by chromophore 5 formed by interaction of a probe with the target lodged in a hole 11, a planar resonator 12 is formed around each hole 11.

Such a resonator can, for example, be constituted by a series of concentric channels (or grooves) 13, opening at the upper surface 24 and with widths and depths selected to provide the properties of confinement and extraction of the light emitted at their center. More precisely, this resonator is arranged so that the electric field has an antinode at the level of hole 11 containing chromophore 5 and so that it stores electromagnetic energy, the light being recovered at the channels (or grooves) 13 then transmitted to the portion located above the surface 24, following (approximately) the arrows, to be captured by a suitable collecting device.

The grooves can be a few micrometers deep or can equal or exceed the radii. The groove width must be equal to about a fraction of the emitted wavelength, typically of the order of 0.1 $\mu$m.

The size of the circular resonator is determined by the following condition:

$$\text{radius} = (\lambda/2\pi n_{eff})*z_{m,n}$$

where $z_{m,n}$ is the $n^{th}$ zero of the Bessel function of order m, $J_m(z)$. This is meant for a resonator with a perfect lateral mirror; $n_{eff}$ is the mode of the subjacent planar guide if it exists, if not it is the index of the solid in which the resonator is defined.

For multilayer mirrors, the presence of an antinode at the edge of the resonator must be taken into account instead of a field node at the edge of a perfect mirror resonator. Thus, a quarter wavelength has substantially to be added:

$$\text{radius} = (\lambda/2\pi n_{eff})*z_{m,n} + \lambda/(4n_{eff}).$$

Preferably, the groove pitch is substantially equal to a multiple of $(\lambda/2\pi n_{eff})$ or very slightly higher (5% to 20%). This choice is suitable for very thin multilayers, $\lambda/8$ to $\lambda/50$, the lower limit usually being fixed by technology. This groove width controls the penetration length of the wave into the circular "mirror".

Other types of planar resonator can be envisaged. Lamellar arrays can be produced with rectangular grooves or parallel grooves with dimensions similar to those mentioned above. A two-dimensional or three-dimensional photonic crystal can also be produced by forming holes or hollow column placed in selected locations in the substrate, at its upper portion 10. As an example, the holes can be round and form a triangular array, omitting a certain number of them to form the resonant cavity.

Such planar resonators (concentric grooves and photonic crystals) are described in the document "Optical and confinement properties of two-dimensional photonic crystals", J. Lightwave Techn., vol. 17, pp. 2063–2077, 1999, H.

Benisty, C. Weisbuch, D. Labilloy, M. Rattier, C. J. M. Smith, T. F. Krauss, R. M. De La Rue, R. Houdré, U. Oesterle and D. Cassagne.

If their dimensions are selected for resonance with chromophore 5, these planar resonators have resonant modes that can remove a large proportion of the emission from this chromophore. These resonant modes are shown highly diagrammatically as the dotted lines in FIG. 5. Further, these planar resonators ensure coherent diffraction, similar to Bragg type diffraction, which can redirect the energy of the resonant mode towards the collecting device.

In a variation, a very small resonator can be used, typically $2\lambda/n$ or $3\lambda/n$. In this case, the resonator can be anti-resonant over the whole wavelength range of chromophore 5, which inhibits emission in the plane and encourages emission along the vertical, i.e., perpendicular to the upper surface 24. Coupling of the photodetecting elements then allows the light to be collected.

In the case of photonic crystal type structures, it is possible to use those known as photon band gap type crystals which have the property of forbidding propagation of light through them, forcing all of the electromagnetic energy of the light emitted by the chromophore 5 outside them, even when the chromophore 5 is located at a distance of several wavelength ($\lambda$) from the interior of the photonic crystal.

When no longer resonant, i.e., when they have sizes or radii of more than about $10\lambda$, the groove structure or photonic crystal type of structure can be used to diffract the light guided from the chromophore. These structures bend towards geometrical optics and function well for a certain variety of incident wavelengths and no longer for one or more overriding modes. This configuration has the advantage of requiring less rigorous dimensional tolerances of the probes in the horizontal position, while in the case of a resonator, the size of the antinode in the electric field must typically be about $\lambda/2n$, i.e., less than about 200 nanometers.

Concentric grooves, lamellar gratings (rectangular, parallel or V shaped grooves or the like) and photonic crystals all have spectral/angular windows in which their behavior is not reflective and can be rendered extractive. Optionally, extraction can be carried out via a substrate, on the back of which microlenses (functioning in accordance with the laws of geometric optics) can be placed to augment the quantity of light collected.

In a further embodiment of the invention, localized resonances are created of the type that occur in surface enhanced Raman scattering. These resonances result from local reinforcement of the electromagnetic field induced by the presence of nanometric structures, such as nanometric islets, or nanometric holes, formed from particular metals such as silver (Ag) or gold (Au). Local reinformcement primarily concerns emission, and also excitation. More precisely, it is possible to use resonances either to reinforce the excitation light ($\lambda_{exc}$), or to couple the light emitted by the chromophores ($\lambda_{emis}$) to collecting means. To this end, it is possible to deposit on a simple substrate, or a structured substrate as described above, irregular films of silver (or organized silver nanostructures) onto which probes are placed. More details of these nanometric structures or holes can be obtained by reference to articles by W. L. Barnes and V. A. Shubin et al., published in IEEE Journal of Lightwave Technology, vol. 17, p. 21–83, November 1999.

Figure 6:
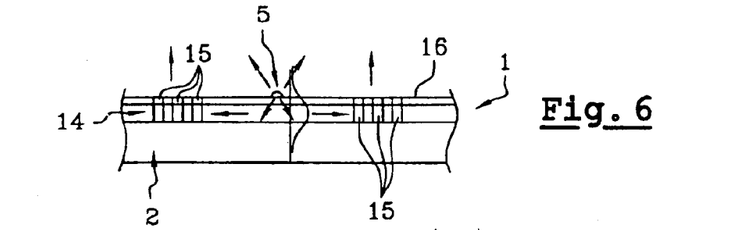
FIG. 6 is a highly diagrammatic cross sectional view of a device in accordance with the invention with a planar resonator and a waveguide.

Reference should now be made to FIG. 6 to describe a further embodiment of a device of the invention, in which the light concentration means also function in accordance with the laws of wave optics.

In this embodiment, a planar waveguide is provided below the portion of the support on which the chromophores 5 are fixed. To this end, for example, it is possible to deposit a high index layer 14 on the upper face of a substrate 2, the index of the high index layer also being higher than that of the upper layer 16 carrying chromophores 5. However, the structure can remain a guiding structure in the absence of the upper layer 16, as the skilled person will know.

More complex guiding structures can be envisaged to position the guided modes of the light emitted by the chromophores in a particular manner, for example so that the field is as strong as possible at the surface. Such a structure can, for example, comprise a substrate 2 with a very low index (no upper layer 16) and a guiding layer with an index and thickness selected at the limit of the mode cutoff condition. More details on this cutting condition can be obtained by reference to Chapter 8 in "Light Transmission Optics" (Van Nostrand, New York 1972) by D. Marcuse.

Such guides can be monomodal or multimodal in type. In this latter case (multimodes), if the number of modes is really high, and as a result, the guide is very thick, then the structure will function in accordance with the laws of geometrical optics. Further, this type of guiding structure can be very restricting or less restricting depending on whether there is a large or small difference in index between the surrounding layers. Further, these guiding structures can be optimized so as to capture a large fraction of the light, either in a single mode, or in an overriding proportion of these modes if they are multimodal, to facilitate light extraction.

When the light concentration means comprise only a guiding structure 14, the guided modes are channeled to the front of the structure. It is then possible to collect the light by coupling the ends of the waveguide to a suitable collecting device, such as fiber optics, or microscope objectives.

It is also possible to focus the collecting device at different depths inside the guiding structure to isolate successive lines of chromophores 5. One example of this type of focusing is described in the document "Use of guided spontaneous emission of a semiconductor to probe the optical properties of two-dimensional photonic crystals", Appl. Phys. Lett., vol. 71, pp. 738–740, 1997, D. Labilloy, H. Benisty, C. Weisbuch, T. F. Krauss, R. Houdré and U. Oesterle.

To allow collection of guided modes on a single side of support 1, groove or channeled structures can be provided around each chromophore and open into the guiding structure, to produce a species of blazed grating that channels the emitted light to a service side of the guiding structure, where detection is made.

As illustrated in FIG. 6, it is also possible to add to the guiding structure 14 a further structure forming a planar resonator, of the type described with reference to FIG. 5. As an example, it is possible to form concentric grooves (or channels) 15 around chromophore 5, to redirect the guided modes via the guiding structure 14 towards a zone located above said chromophores 5.

In a variation, it is possible to replace the grooves or channels 15 by a two-dimensional or three-dimensional photonic crystal constituted by holes or columns, as described above.

Reference should now be made to FIG. 7 to describe a further embodiment of a device according to the invention, also functioning in accordance with the laws of wave optics.

In this embodiment, the device of the invention comprises a substrate 2 the upper portion 10 of which is formed with relief structures 6, with recesses or bosses. Preferably, these structures 6 are channels or ribs that are linear and parallel to each other, for example in the form of a U or a V (as in the example shown). The size of these structures is of the order of the working wavelength. The probes can be placed either at the top of the structures (as shown) or at the bottom of the structures, i.e., in the space joining the lower portions of structures 6. It is also possible to associate metals with dielectric supports, for example by depositing patterns of metal over all or some of the ribs or grooves.

As is known by the skilled person, at certain locations, in particular their top, such structure induce channeling effects on the light (see the arrows in FIG. 7). As a result, by placing the photodetecting elements (or pixels) 17 below the relief structures 6 on which chromophores 5 are fixed, it is possible to harvest the photons emitted by the chromophores into the structures and channeled thereby. The light emitted in the direction substantially opposite to the direction of the channeled light can be collected by other photodetectors placed above chromophores 5. As indicated above, these photodetecting pixels can be CCD elements forming a detection matrix, for example.

Figure 8:
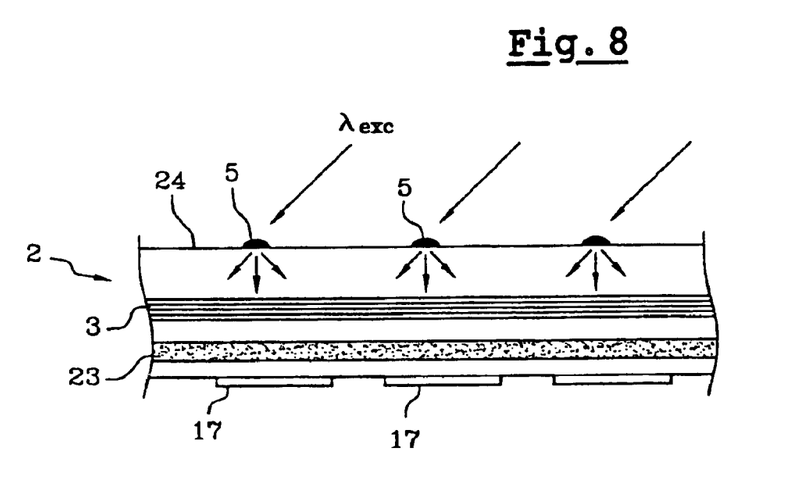
FIGS. 8 to 14 are highly diagrammatic cross sectional views of different variations of the device in accordance with the invention.

Integration of a CCD photodetecting matrix 17 with a substrate 2 carrying chromophores 5 is shown more completely in FIG. 8, which shows that substrate 2 comprises, below chromophores 5, reflective means 3 with a multilayered structure, and an absorbent layer 23 that is insensitive to angle of incidence and located between reflective layers 3 and photodetectors 17. The reflective layers 3 ensure a maximum excitation and emission field at the chromophores and prevent the excitation light from propagating by simple transmission and by diffusion towards the photodetecting matrix 17. The absorbent layer 23, as used for RGB filters in photography and in color CCD arrays, has an absorption band and thickness selected to reduce cross-color and/or enhance the signal-to-noise ratio at photodetectors 17. This produces a gain of 10 or 100 times as regards extinction of the excitation light, without greatly degrading collection of the fluorescence emitted by chromophores 5.

These improvements also apply to an embodiment of the invention where the CCD detector is not integral with substrate 2 carrying chromophores, but located at a sufficiently small distance for each chromophoric element to be facing sufficiently well defined pixels.

Figure 9:
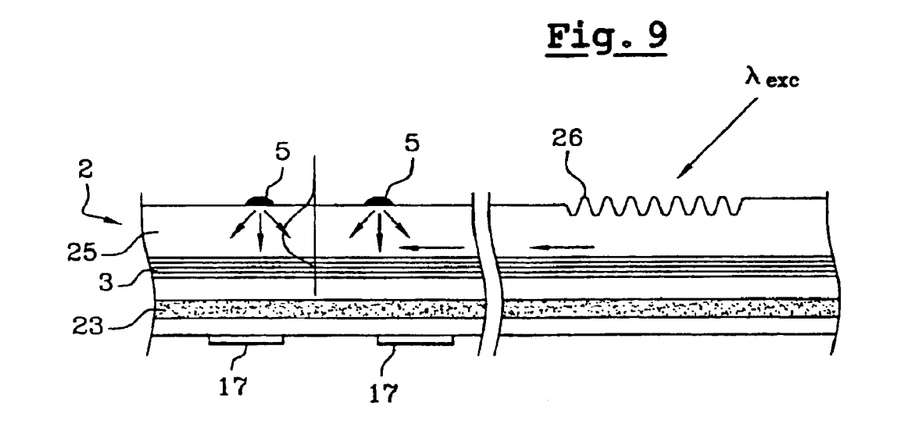

In the variation shown in FIG. 9, chromophores 5 carried by substrate 2 are excited by a damped wave. To this end, substrate 2 comprises a guiding layer 25 analogous to the layer 14 in FIG. 6, with an index that is higher than that of the surrounding layers and wherein the upper face is very close to chromophores 5 on the scale of the wavelength of the damped wave of the guided wave. The guiding layer 25 is edge lit (after cleaving or cutting and polishing) or by means of a grating (for example, a thin layer 26 of photosensitive resin on the guiding layer in a neutral zone of substrate 2, with a low thickness modulation of 1 to 100 nm, allowing light to be coupled by illumination using a laser with a suitable coupling angle determined by applying the law of gratings. Regarding the remainder, the device of FIG. 9 contains reflective layers 3 and absorbent layers 23 that have already been described with reference to FIG. 8.

In a variations chromophores with different colors are detected. The chromophores are illuminated by one or more excitation wavelengths $\lambda_{exc1}$ and possibly $\lambda_{exc2}$ and in response, emit two wavelengths, respectively $\lambda_{fluo1}$, $\lambda_{fluo2}$. In this case, it is possible to recover separately the signals for each color on pixels or close groups of pixels all each chromophores 5 using wavelength filters such as those described above, but individualized to each pixel or group of pixels. In addition to detecting two colors, this can use the advantages of differential treatment of the signals from the two colors. The principle extends to several colors.

Figure 10:
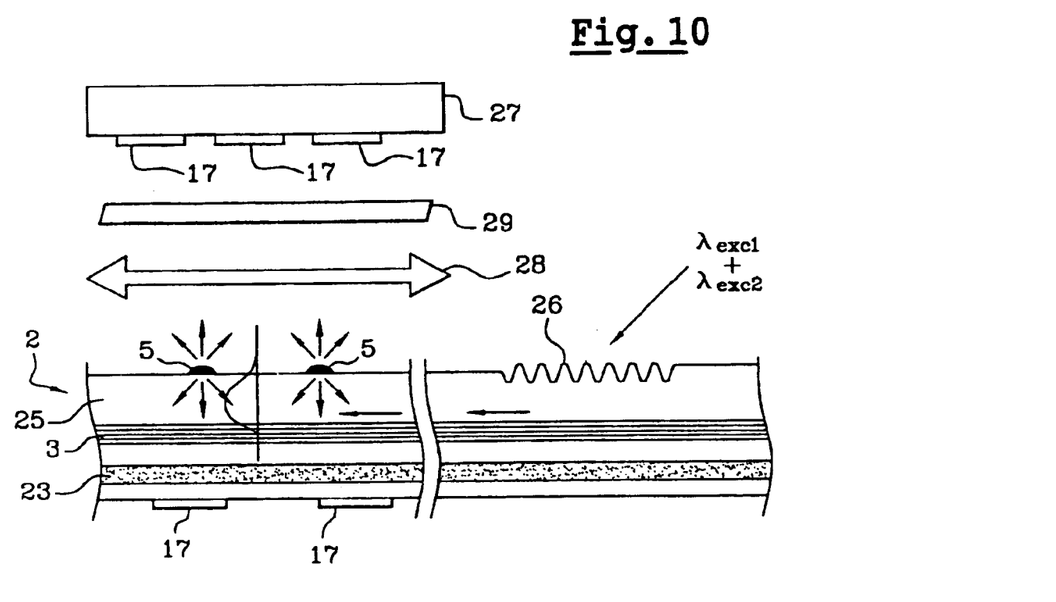

A further embodiment, shown diagrammatically in FIG. 10, allows the detection of chromophores with different colors at each point 5 on substrate 2. The device is reminiscent of that of FIG. 9 and additionally comprises a second matrix 27 of CCD photodetectors 17 placed above the chromophores, interposing an objective 28 and a rejecting filter 29 between the chromophores and the second matrix 27. The chromophores 5 are illuminated by two excitation wavelengths $\lambda_{exc1}$ and $\lambda_{exc2}$ and in response, emit two wavelengths, respectively $\lambda_{fluo1}$, $\lambda_{fluo2}$. The absorbent layer 23 of substrate 2 form a spectral filter for rejecting excitation wavelengths and one wavelength $\lambda_{fluo2}$ emitted by chromophores 5, by allowing the other wavelength $\lambda_{fluo1}$ emitted by chromophores 5 to pass through. Filter 29 associated with the second matrix 27 stops the excitation wavelengths and the wavelength $\lambda_{fluo1}$ emitted by chromophores 5, allowing the wavelength $\lambda_{fluo2}$ to pass through. If necessary, an absorbent layer 23 of the type described above can be associated with filter 29.

A variety of light collecting devices are diagrammatically shown in FIGS. 11 to 16 by way of example only.

Figures 11, 12:
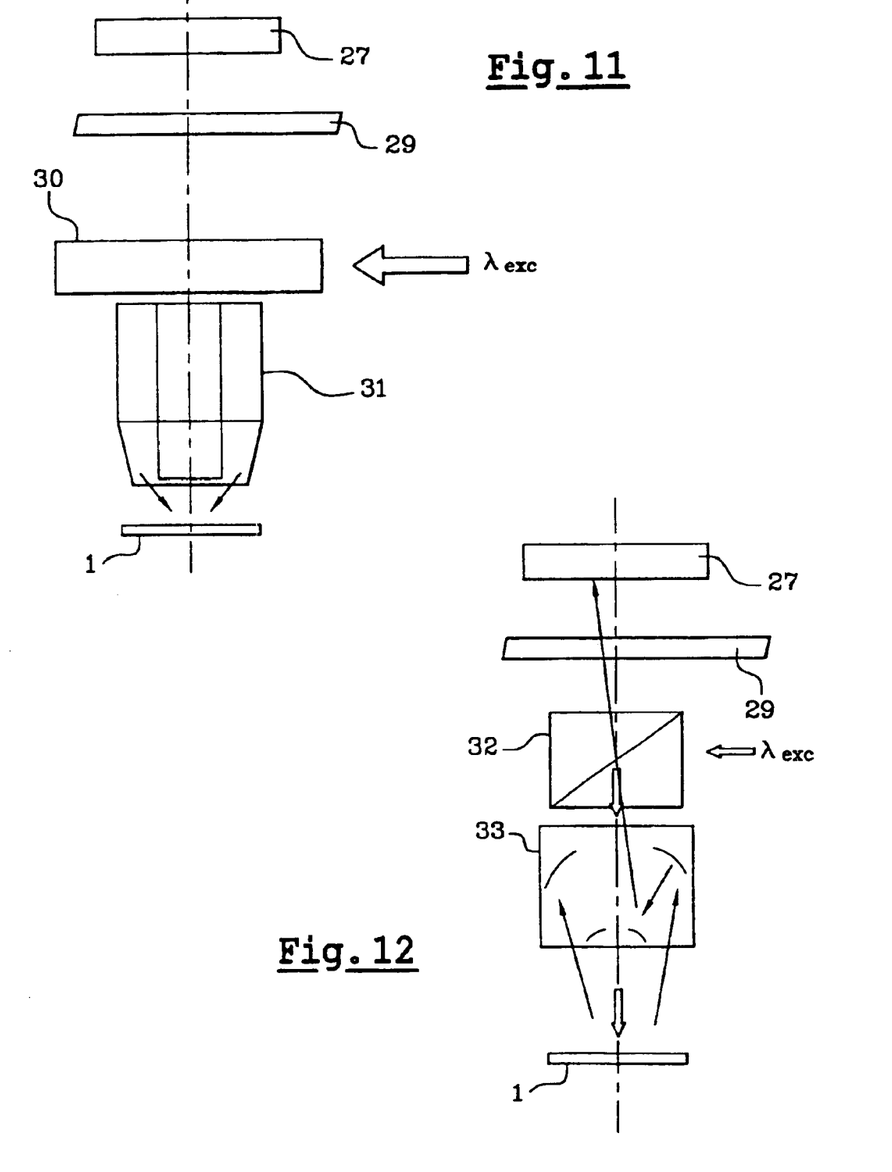

The collecting device in FIG. 11 comprises a CCD type photodetecting matrix 27 or the like receiving the luminescence emitted by the chromophores carried by support 1, passing through a filter 29 for rejecting excitation light and stray luminescence emitted by support 1. Excitation of chromophores by a wavelength $\lambda_{exc}$ takes place at a non zero angle of incidence with respect to the normal to the support 1, by means of a dark field type coupler, routinely used in episcopy and metallography, placed between the support 1 and filter 29. It receives the excitation light from the side and returns it towards the support at angles of incidence that are higher than the numerical aperture of objective 31. Objective 31 collects the luminescence emitted by chromophores in the direction perpendicular to support 1.

In the variation shown in FIG. 12, we see the photodetector matrix 27 and filter 29 of the device of FIG. 11, and support 1 is illuminated by a separator cube 32 associated with a mirror objective 33 of the Cassegrain type (Cassegrain-Schmitt) which encourages detection at a non zero angle with respect to the normal to support 1, as shown by the arrows. Excitation passes via a central opening formed in the reflecting mirror of the objective and falls on support 1 with an almost normal angle of incidence.

Figure 13:
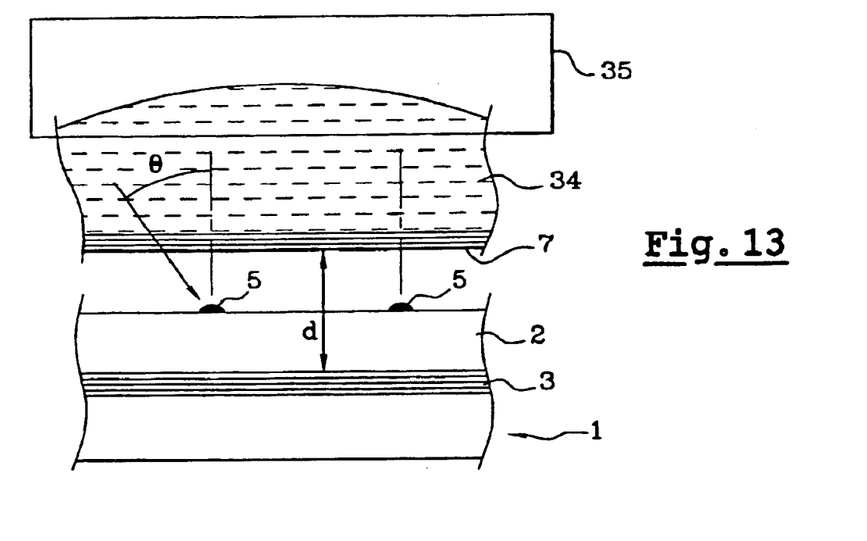

The collecting device of FIG. 13 corresponds to that described above with reference to the resonant cavity of FIG. 4A: in this device, the second mirror 7 is formed on the lower face of the entrance lens 34 of an objective 35 of the collecting device. The optical path between mirrors 3 and 7 is a multiple of $\lambda_{fluo}/2$.

Figure 14:
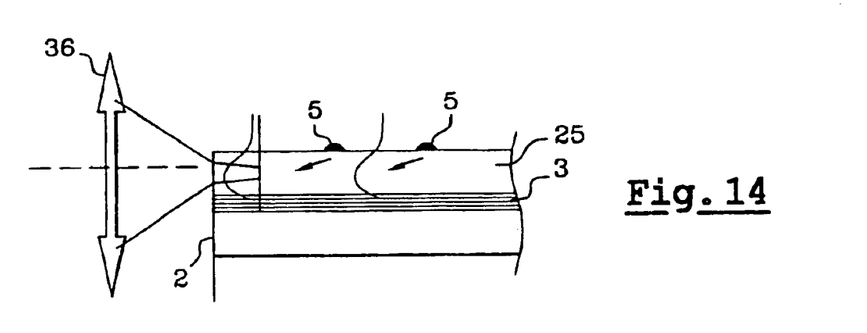
Figure 15:
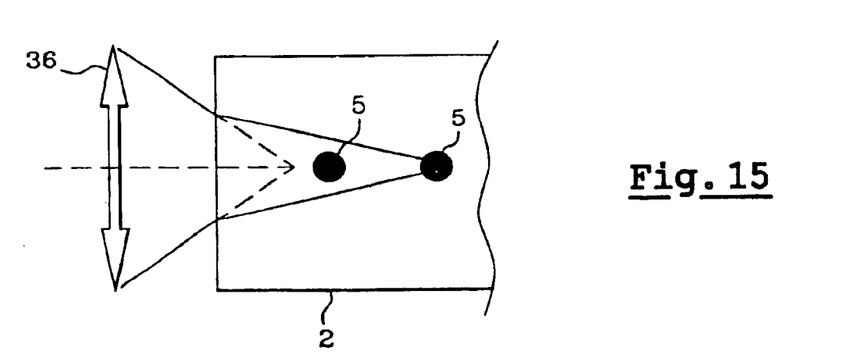
FIG. 15 is a highly diagrammatic cross sectional view of the top of the device of FIG. 14.

In the device of FIGS. 14 and 15, which corresponds to the embodiment of FIG. 6, luminescence emitted by chromophores 5 into an upper guiding layer 25 of substrate 2 is recovered at one end by an objective shown at 36. FIG. 16 shows the situation in which the guide points matching with the detector encourage selective detection of one of the chromophores on which focusing is better, compared with the others, in which emission is not in the focal plane and is not concentrated in the detector (or in the pixel in the detector matrix), which allows discrimination between the chromophores located at different distances from the edge of the guide.

What is claimed is:

1. A device for supporting chromophoric elements, comprising a substrate having an upper face on which said chromophoric elements are fixed and means for enhancing the quantity of light emitted by the chromophoric elements toward a collecting device, maid means being selected from a group consisting of:
- reflective means placed in the substrate at a distance from said upper face;
- microlenses each associated with a chromophoric clement and functioning in transmission or in reflection;
- diffraction means placed at a distance from the chromophoric elements and functioning in transmission or in reflection;
- first mirror means and second mirror means parallel to each other and placed on either side of the chromophoric elements to define an asymmetric resonant cavity;
- a planar wave guide formed in the substrate below the upper face carrying the chromophoric elements, to capture a portion of the light emitted by the chromophoric elements into the substrate and/or to supply excitation light;
- a configuration of the upper face of the substrate, formed as wells with a reflective bottom and filled with a material with a suitable index each receiving a chromophoric element; and
- planar resonators formed in the upper face of the substrate.

2. A device according to claim 1, wherein said reflective means are placed at a distance (d) from the upper face, this distance (d) satisfying the relationship $d > n\lambda/2NA^2$.

3. A device according to claim 1, wherein said microlenses are formed in a layer of the substrate at a distance from each chromophoric element and arranged to focus the light emitted into the substrate toward the collecting device.

4. A device according to claim 1, wherein said diffraction means are formed in a layer of the substrate at a distance from the chromophoric elements and arranged so as to diffract the light emitted into the substrate towards the collecting device.

5. A device according to claim 1, wherein said first mirror means is integral with the substrate and said second mirror means is a semi-reflective mirror placed facing the chromophoric elements, substantially parallel to the first mirror means and at a distance therefrom selected to define said asymmetric resonant cavity, in particular of the Fabry-Perot type, and arranged to deliver the emitted light to the collecting device by transmission.

6. A device according to claim 5, wherein the second mirror means is formed on an entrance face of an objective of the collecting device.

7. A device according to claim 5, wherein the second mirror means is formed on an entrance face of a microscope observation coverslip.

8. A device according to claim 1, wherein said asymmetric resonant cavity, is of the Fabry-Perot type, is integrated in the substrate, and is placed below an upper layer, which is at least partially permeable, vertically and/or laterally, to allow migration of the chromophoric elements towards sites selected inside the resonant cavity.

9. A device according to claim 8, wherein said cavity is defined by said first and second mirror means.

10. A device according to claim 9, wherein at least one of the mirror means is constituted by a multiplicity of dielectric layers.

11. A device according to claim 10, wherein the dielectric layers are produced from materials selected from the group formed by semiconductors, oxides, glasses, nitrides, organic polymers or organometallic polymers.

12. A device according to claim 11, wherein the polymers are selected from the group formed by amorphous polymers and "orientated" and birefringent polymers.

13. A device according to claim 8, wherein said upper layer is produced from a porous material, in particular silica gel.

14. A device according to claim 8, wherein the upper layer comprises holes at selected locations, to encourage migration of chromophoric elements towards said sites.

15. A device according to claim 1, wherein the upper face of the substrate has a n-dimensional structure, n being a whole number equal to 2 or more, with dimensions selected as a function of the wavelength of the emitted light.

16. A device according to claim 15, wherein said structure comprises a multiplicity of parallel linear three-dimensional structures, selected from the group formed by channels and ribs, which are U shaped or V shaped or parabolic or elliptical in shape.

17. A device according to claim 16, wherein each of the tops or interstices of the parallel linear three-dimensional structures can receive chromophoric elements.

18. A device according to claim 16, wherein at least a portion of the space separating said parallel linear three-dimensional structures comprises a reflective material above which is placed a filler material with a selected index, said chromophoric elements being intended to be placed on said filler material or on the tops of the three-dimensional structures.

19. A device according to claim 15, wherein said structure comprises a two-dimensional or three-dimensional array of holes or columns, defining a photonic crystal and resonant cavities associated with the chromophoric elements.

20. A device according to claim 19, wherein said photonic crystal is of the photon band gap type.

21. A device according to claim 15, wherein said structure comprises a multiplicity of three-dimensional wells, filled with a material having a high index with a reflective material interposed at the bottom of each well and each well being capable of receiving at least one chromophoric element on said filling material.

22. A device according to claim 21, wherein the configuration of the three-dimensional wells is selected from the group formed by parabolas of revolution, ellipses of revolution, and n-dimensional facets, n being a whole number equal to 1 or more.

23. A device according to claim 15, wherein said structure comprises, for each chromophoric element, one of said planar resonators capable of storing electromagnetic energy from the field it induces and arranged so that the associated chromophoric element is positioned substantially at the antinode of said electromagnetic field.

24. A device according to clam 23, wherein the planar resonator comprises at least two three-dimensional concentric circular channels, said chromophoric element being placed substantially in the center of said channels.

25. A device according to claim 23, wherein the planar resonator comprises a multiplicity of three-dimensional channels defining a lamellar grating, the chromophoric elements being placed substantially at the center of said lamellar grating, and said channels having a form selected from the group formed by rectangular shapes and parallel linear shapes.

26. A device according to claim 23, wherein said planar waveguide is placed substantially below the chromophoric elements and arranged to collect the light emitted by said chromophoric elements in the direction of support means and guide it in the direction of the planar resonator.

27. A device according to claim 1, wherein said group comprises means capable of ensuring localized resonances by local reinforcement of the electromagnetic field induced by the presence of nanometric holes, which may or may not be regular, produced in selected metals, in particular in silver (Ag) or gold (Au).

28. A device according to claim 27, wherein said nanometric holes or structures are arranged to locally enhance emission and/or excitation, by a mechanism of the type occurring in surface enhanced Raman scattering.

29. A device according to claim 27, wherein the upper face of the substrate comprises an irregular film of silver or a multiplicity of organized silver nanostructures, said film or said nanostructures being capable of receiving chromophoric elements.

30. A device according to claim 1, wherein the substrate is associated with a matrix of charge coupled (CCD) light detection elements, at least some of these detection elements being capable of being electronically addressed in correspondence with at least one chromophoric element.

31. A device according to claim 30, wherein certain detection elements are associated with zones having a reference activity signal, such that a differential measurement can be carried out between detection elements associated with chromophoric elements and detection elements associated with reference zones.

32. A device according to claim 31, wherein to detect the chromophoric elements emitting over at least two different wavelengths, the device comprises wavelength filtering means selectively associated with said detection elements for detecting two emitted wavelengths and for differential treatment of exit signals from said detection elements.

33. A device according to claim 30, wherein said reflective means are arranged within the substrate to reject light intended to excite the chromophoric elements.

34. A device according to claim 33, comprising an absorbent layer that is insensitive to the angle of incidences located between the matrix of detection elements and said reflective means.

35. A device according to claim 1, wherein the collecting device comprises a matrix of photodetectors arranged above the upper face of the substrate carrying the chromophoric elements and receiving light emitted by the chromophoric elements through a filter for rejecting excitation light.

36. A device according to claim 1, comprising two photodetector matrices placed respectively below and above the chromophoric elements and associated with rejection filters for receiving the light emitted by the chromophoric elements over two distinct wavelengths.

37. A device according to claim 1, wherein said planar waveguide is placed substantially below the chromophoric elements and arranged to collect the light emitted by said chromophoric elements in the direction of the substrate and to guide it towards the collecting device.

38. A device according to claim 37, wherein the waveguide comprises channels close to each chromophoric element, said channels defining a blazed grating arranged to direct the light collected by the waveguide towards the collecting device.

39. A device according to claim 1, wherein said planar waveguide supplies exitation light to the chromophoric elements.

40. A device according to claim 39, wherein the planar waveguide comprises, in a neutral zone of the substrate, a grating with a low thickness modulation for coupling the excitation light.

41. A device according to claim 1, wherein the chromophoric elements are selected from the group formed by molecules that can emit chromophoric or chromogenic signals and semiconductor nanostructures bound to the upper face of the substrate and capable of receiving a probe (respectively a target) that can interact with a target (respectively a probe).

42. A device according to claim 1, wherein the chromophoric elements are couples comprising a target (respectively a probe) having interacted with a probe (respectively a target) integral with the upper face of the substrate.

43. A device according to claim 1, wherein said reflective means are at a distance d from the upper face, the distance d satisfying the relationship $d < n\lambda/2NA^2$ and being selected to ensure the presence of a field antinode of the emitted light at the upper face on which the chromophoric elements are fixed.

44. A device according to claim 43, wherein the substrate is arranged to receive excitation light intended to excite chromophoric elements at an angle of incidence with respect to the normal to the upper face, said distance d and the angle of incidence of the excitation light being selected to ensure the presence of a field antinode of the excitation light at the upper face of the substrate.

45. A device according to claim 43, wherein said reflective means comprise a metallic layer.

46. A device according to claim 43, wherein said reflective means comprise a plurality of dielectric layers.

47. A device according to claim 1, wherein said reflective means comprise a plurality of dielectric layers.

* * * * *

UNITED STATES PATENT AND TRADEMARK OFFICE
CERTIFICATE OF CORRECTION

PATENT NO. : 6,867,900 B2
DATED : March 15, 2005
INVENTOR(S) : Weisbuch et al.

It is certified that error appears in the above-identified patent and that said Letters Patent is hereby corrected as shown below:

Column 1,
"PGT" should read -- PCT --.

Column 10,
"PGT" should read -- PCT --.

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,867,900 B2
DATED : March 15, 2005
INVENTOR(S) : Weisbuch et al.

It is certified that error appears in the above-identified patent and that said Letters Patent is hereby corrected as shown below:

Column 1,
Line 5, "PGT" should read -- PCT --.

Column 10,
Line 43, after "possible" insert -- integers --.

Column 11,
Lines 22 and 23, the formula should read as follows:
-- $d1=(m+½)*a_{fluo}-a_{pen}(\lambda_{fluo})$ --.

Column 17,
Line 1, "maid" should read -- said --.
Line 5, "clement" should read -- element --.

Signed and Sealed this

Sixth Day of December, 2005

JON W. DUDAS
*Director of the United States Patent and Trademark Office*